United States Patent [19]

Nappholz et al.

[11] Patent Number: 4,901,725
[45] Date of Patent: Feb. 20, 1990

[54] MINUTE VOLUME RATE-RESPONSIVE PACEMAKER

[75] Inventors: Tibor A. Nappholz, Englewood; John R. Hamilton, Littleton; James C. Hansen, Denver, all of Colo.

[73] Assignee: Telectronics N.V., Curacao, Netherlands

[21] Appl. No.: 150,038

[22] Filed: Jan. 29, 1988

[51] Int. Cl.$^4$ .............................................. A61N 1/00
[52] U.S. Cl. ........................... 128/419 PG; 128/734; 128/725
[58] Field of Search ............. 128/419 P, 419 PG, 725, 128/716, 720, 734, 718, 723

[56] References Cited

U.S. PATENT DOCUMENTS

| 4,440,177 | 4/1984 | Anderson et al. | 128/725 |
|---|---|---|---|
| 4,444,201 | 4/1984 | Itoh | 128/725 |
| 4,513,752 | 4/1985 | Weyant | 128/419 PG |
| 4,585,004 | 4/1986 | Brownlee | 128/419 PT |
| 4,596,251 | 6/1986 | Plicchi et al. | 128/419 PG |
| 4,702,253 | 10/1987 | Nappholz et al. | 128/419 PG |
| 4,721,110 | 1/1988 | Lampadius | 128/419 PG |
| 4,730,618 | 3/1988 | Lekholm et al. | 128/419 PG |
| 4,730,619 | 3/1988 | Koning et al. | 128/419 PG |
| 4,757,815 | 7/1988 | Standberg et al. | 128/716 |

FOREIGN PATENT DOCUMENTS

| 34303 | 9/1983 | Austria | 128/419 PG |
|---|---|---|---|
| 0140472 | 5/1985 | European Pat. Off. | 128/419 PG |
| 0228985 | 7/1986 | European Pat. Off. | 128/734 |
| 0249821 | 12/1987 | European Pat. Off. | 128/419 PG |

OTHER PUBLICATIONS

A. Barker et al., "Single Impedance Pneumograph and Volume Integrator" Technical Note Medical and Biological Engineering, May, 1973, pp. 352–353.

Primary Examiner—Francis Jaworski
Assistant Examiner—George Manuel
Attorney, Agent, or Firm—Gottlieb, Rackman & Reisman

[57] ABSTRACT

A rate-responsive pacemaker whose rate control parameter is minute volume derived over a bipolar lead. An algorithm based on averaged samples and zero crossings provides enhanced accuracy. Sustained exercise at high pacing rates is possible.

19 Claims, 3 Drawing Sheets

RESPIRATORY IMPEDANCE

RESPIRATORY IMPEDANCE MAGNITUDE

RESPIRATORY IMPEDANCE AVERAGE

SAMPLES AT ZERO CROSSINGS

SAMPLE AVERAGE

MINUTE VOLUME RATE-RESPONSIVE PACEMAKER

DESCRIPTION

This invention relates to rate-responsive pacemakers, and more particularly to such pacemakers in which the rate control parameter is minute volume.

In U.S. Pat. No. 4,702,253, in the names of Nappholz et al, there is disclosed a rate-responsive pacemaker for which the rate control parameter is minute volume. Minute volume is a measure of the amount of air breathed in as a function of time; the greater the amount of air which is breathed in, the greater the need for a higher pacing rate. Minute volume is measured in the pacemaker of the aforesaid patent (hereinafter referred to as the "Nappholz et al pacemaker") by providing a three-electrode lead. One of the electrodes is used in a conventional manner for sensing an electrogram signal and pacing the patient's heart. The other two electrodes are used for the minute volume measurement. The two electrodes are in a blood vessel in the vicinity of the patient's pleural cavity. Current pulses are periodically applied between one of the electrodes and the pacemaker case. The voltage between the other electrode and the pacemaker case is measured, and the voltage measurement is a function of the blood impedance in the vessel. The blood impedance is, in turn, dependent upon the pleural pressure. The modulation in the impedance measurement thus can be used to determine the minute volume. The degree of the impedance change during the course of each breath represents the tidal volume (the volume of air contained in each breath); and by summing the individual tidal volume measurements over a fixed period of time, thereby introducing breathing rate as a factor, the minute volume can be derived.

One problem with most rate-responsive pacemakers in general is that the rate control parameter (temperature, Q-T interval, blood oxygen content, etc.) can vary slowly over time for reasons having nothing to do with metabolic demand; such changes should not be reflected as permanent changes in pacing rate. For example, in the Nappholz et al pacemaker if the pacemaker lead happens to shift in position and there is a permanent bias in the blood impedance measurement, then there should not be a permanent bias in the rate. Similarly, long-term drug-induced changes in the measurement of any rate control parameter should be balanced out in some way so that whatever measurement is involved reflects true metabolic demand and is not influenced by extraneous factors.

The basic technique employed in the Nappholz et al pacemaker to overcome extraneous effects on the minute volume measurement is based on the recognition that stress-related (including exercise-related) changes in the minute volume measurement are relatively fast, while the extraneous factors occur more slowly. What is done is to derive two average values of minute volume, one a short-term value which represents changes in stress level and another a long-term value which can serve as a baseline for variations in the short-term value. By subtracting one from the other and using the difference for rate control, long-term effects (which are reflected in both averages) are canceled out, and only short-term effects remain.

One problem with this approach is that there are patients who may exercise for very long periods of time. When such a patient first starts exercising, his short-term average value of minute volume increases rapidly relative to his long-term average value of minute volume, and the pacemaker rate increases. But as time goes by and the long-term average increases as well, the difference between the two values decreases, and the net result is that the pacemaker rate may drop down all the way to the minimum rate—even though during periods of peak exercise what might be desired is pacing at the maximum rate. It is an object of the present invention to prevent such a reduction in pacemaker rate during lengthy periods of stress or exercise.

Another problem with the Nappholz et al pacemaker has to do with the algorithm for deriving minute volume from the impedance measurement. It might be thought that there would be a problem in distinguishing between minute volume and stroke volume. (It has been suggested in the prior art to use the volume of blood in each heartbeat—stroke volume—as a measure of metabolic demand.) Since the two electrodes used to effect the minute volume measurements are in a blood vessel, typically a heart chamber, it might be thought that the blood impedance would be a function of stroke volume as well as minute volume. In fact, the blood impedance is a function of both, but the measurement is primarily dependent on minute volume only. The reason for this has to do with the filter which is used in the measurement channel.

It is rare that a patient breathes at a rate as high as 60 breaths per minute, but it is apparent that high breathing rates do approach low heartbeat rates, e.g., 60 beats per minute and lower. In the usual case, however, there are two or more heartbeats for each breath. What this means is that in a blood impedance waveform there is a relatively high-frequency ripple due to heartbeats superimposed on the relatively low-frequency breathing signal. With an appropriately low passband, a filter can reject for the most part the effects of stroke volume in the measurement signal. Thus what would appear to be a problem, distinguishing between stroke volume and minute volume, is in fact of little concern.

The problem with the impedance measurement in the Nappholz et al pacemaker has to do with the integration technique employed. The blood impedance measurement signal is processed by integrating it over half cycles of the same polarity. All samples of a particular polarity are added together. Since samples are taken at a fixed rate, the integral reflects not only the magnitude of each breath (amplitudes of samples) but also the rate at which breathing is taking place (how often large-value samples occur). This technique provides an adequate representation of minute volume if the shape of the impedance signal is that of a square wave; in fact, if the sampling rate is high enough, the resulting signal will represent exactly the area of the waveform either above the baseline or below it. But if a sinusoid is more characteristic of the breathing signal, then the resulting measurement, while it does reflect the average magnitude of the breaths, does not reflect the frequency at which the breaths occur. This is because the area of a sinusoid over a half cycle is the same no matter what the frequency of the sinusoid. To the extent that a signal representative of breathing approaches a sinusoid, integrating it over half cycles of one polarity cannot provide a measure of minute volume, but rather tidal volume only. While the measurement signal is in fact not sinusoidal in nature, it is apparent that to whatever extent sinusoidal components are present, the Nappholz et al technique does not provide maximum accuracy. It is another object of our invention to provide an improved measurement algorithm for a minute volume rate-responsive pacemaker.

A third problem with the prior art pacemaker is that it was believed to require a lead having at least three electrodes. Bipolar leads are standard in the art. There are many patients with implanted bipolar leads, and if a three-electrode lead is required for a new pacemaker, then a prior art non-rate-responsive pacemaker cannot be replaced by a rate-responsive pacemaker simply by exchanging pacemakers but using the same lead. Furthermore, there are physicians who like the feel of the leads they have been using in the past, and one factor which weighs against implanting a rate-responsive pacemaker might be that it requires a lead with a new feel. It is another object of our invention to provide a minute volume rate-responsive pacemaker which can be used with a conventional bipolar lead.

The pacemaker of our invention solves the problem of the short-term and long-term values of minute volume approaching each other (with the difference thus approaching zero) during periods of sustained exercise by freezing the long-term value when the difference between the short-term and long-term values exceeds a threshold. When the patient starts to exercise, his short-term measurement value increases. The difference between it and the long-term value thus increases, and so does the rate of the pacemaker. If the increase is due to a factor which has a more permanent effect, such as a change in lead position, then the long-term average will also eventually change and the difference between the two values will drop down, thus causing the rate to decrease. That is as desired. (The fact that for some period of time the pacing rate was higher than it had to be is unavoidable, but is not dangerous.) But if the increase in the short-term value was really due to the patient starting to exercise, and if he continues to exercise for a long time, it is desired that the long-term value not increase all the way up to the short-term value, and thus cause a gradual decrease in the pacing rate even though the patient is still exercising. This is avoided in the invention by freezing the long-term value as soon as, and for as long as, the difference between the two averages exceeds a threshold limit. The difference will thus remain high following the start of exercise until it is finished, and there will be sustained pacing at a high rate. (Extraneous factors such as lead shifts and drugs have been shown during clinical testing not to result in a difference value which exceeds the threshold. Consequently, even though the pacing rate may initially increase when it need not, it returns to lower values as the long-term average catches up to the short-term average.)

The problem of deriving an accurate measurement of minute volume is solved by operating on digital samples of the impedance signal in two branches. In a first, the digital samples are converted to absolute magnitudes, and their average value is derived. In the second, the signs of successive digital samples are compared in order to detect the presence of zero crossings. In the illustrative embodiment of the invention, samples are processed at the rate of 20 per second, and the test for a zero crossing is whether 70% of the last ten samples have changed sign from the sign of the signal subsequent to the last zero crossing. Whenever a zero crossing is sensed, a sample of the average value of the absolute magnitude is taken, and the sample is used to update both the short-term and long-term measurement values from which the difference signal which controls the rate is derived. The average value of the absolute magnitudes is directly proportional to the amplitude of the impedance signal and it is thus a measure of the tidal volume; it is an accurate measurement because the effects of noise are canceled (positive balances negative) in the average value. Because the zero crossing detector is relatively immune to noise in that short excursions above or below the baseline are ignored, a sample of the average value is used to update both minute volume measurements for every breath of the patient. The net effect is that the short-term and long-term average values more faithfully represent past history of the patient's minute volume.

With respect to how a conventional bipolar lead can be used in a minute volume rate-responsive pacemaker, it is not so much a question of why a bipolar lead works as it is why it was believed that it would not work. A conventional bipolar lead with tip and ring electrodes is used in the preferred embodiment of the invention. The tip electrode, in contact with the wall of the patient's heart, is used for sensing and pacing; it is also used for measuring the blood impedance between the tip and the case. The current pulse which is used during each measurement cycle flows between the ring electrode and the case. In the above-identified Nappholz et al patent, three-electrode and four-electrode arrangements were described. The reason that it was believed that a two-electrode lead could not be used for all functions is the following.

There have been four-electrode arrangements in the prior art for measuring blood impedance. Consider four electrodes arranged in a line, with current flowing between the two outer electrodes and a voltage measurement taken across the two inner electrodes. In such an arrangement, the current flows the entire way from one voltage-measuring electrode to the other. It was believed that the current used to perform the measurement had to flow along the entire path between the two electrodes across which the voltage measurement is taken.

If we now take a bipolar electrode which is to be used for both pacing/sensing and the impedance measurement, and if the current is to be applied at one electrode and the voltage measurement is to be taken at the other, the case has to be the reference point. (There is no other reference which could be used.) The question is whether the current should be applied between the case and the tip or the ring, with the voltage measurement being taken between the case and the ring or the tip. In accordance with prior art thinking, the current should flow between the tip and the case, so that the path across which the voltage measurement is taken, the end points of which are the ring and the case, is wholly contained within the current path. This is not practical, however, because if current pulses are applied to the tip, they may affect the long-term pacing threshold or precipitate arrhythmias. The only alternative is to apply the current between the ring and the.case, but this would entail taking a voltage measurement between the tip and the case, two points separated by a distance greater than that of the current path. It was just not believed that such a voltage measurement would accurately reflect the blood impedance, and thus provide an indication of minute volume. That a conventional bipolar lead actually works is verified by observing in operation the recently introduced Meta-MV pacemaker of the assignee of this invention. The reason is believed to be that the tip and ring are close together in the low-inpedance blood pool so that the voltage at the tip is similar to that at the ring, even though the tip is not between the ring and case.

Further objects, features and advantages of the invention will become apparent upon consideration of the following detailed description in conjunction with the drawing, in which.

Figure 1:
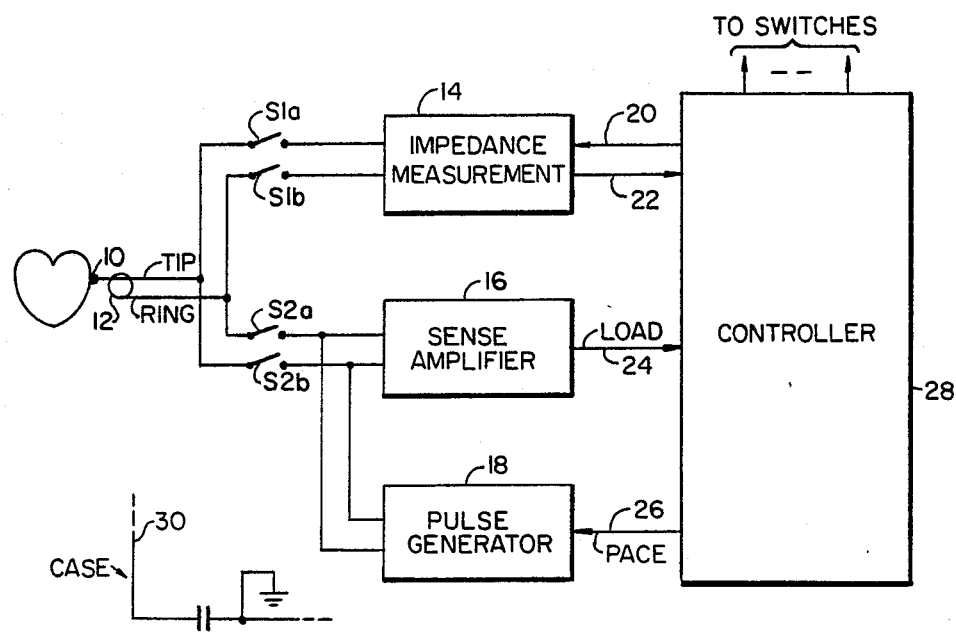
FIG. 1 is a block diagram of the illustrative embodiment of the invention.
Figure 3:
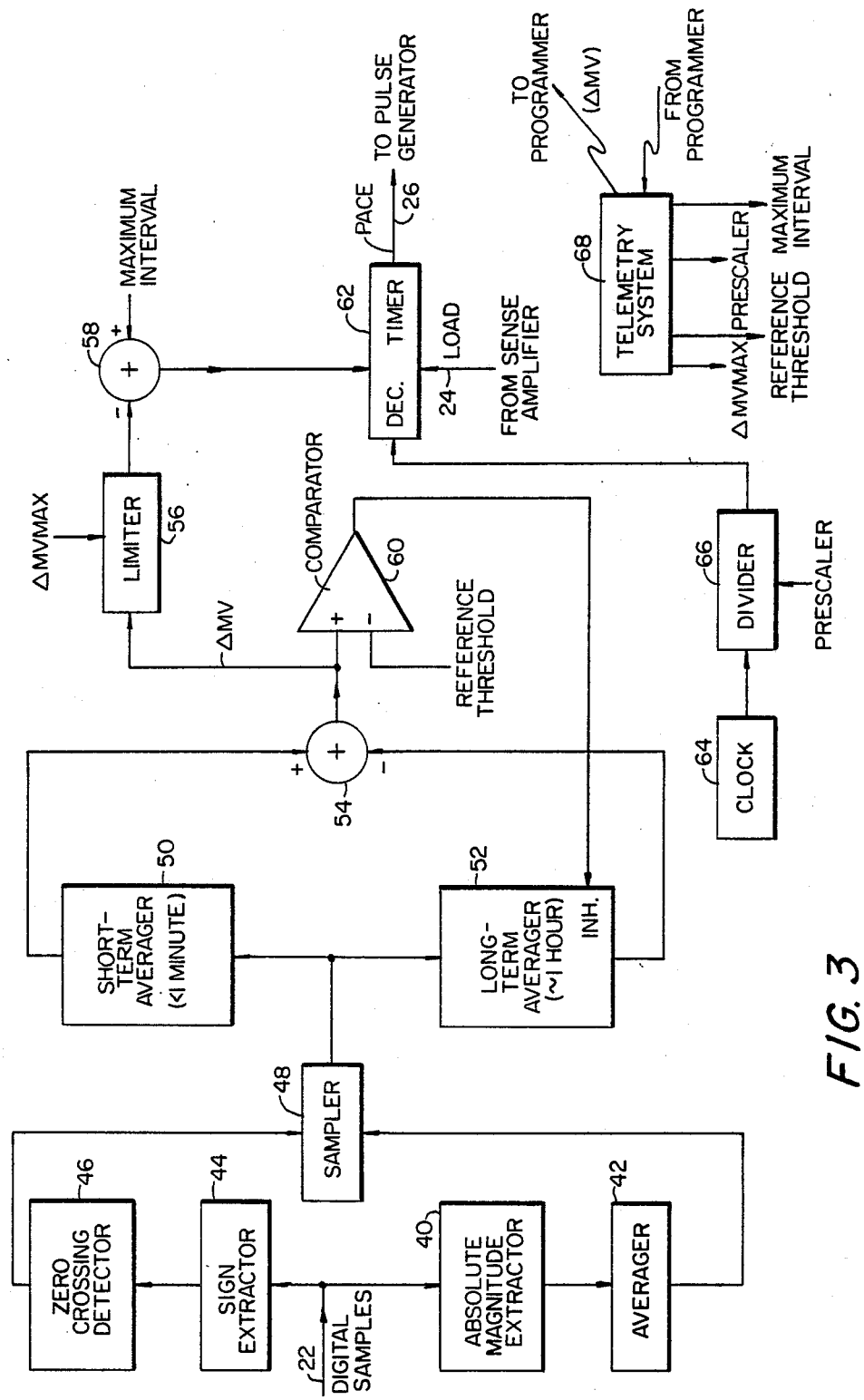
FIG. 3 depicts those circuit blocks contained in controller 28 of FIG. 1 which operate on digital samples of the impedance measurement to derive pace commands for extension to pulse generator 18.

The drawing of FIG. 1 is a high-level block schematic. Tip and ring electrodes 10, 12 are those found in a conventional bipolar lead. All pacemaker logic is under control of controller 28 (which may include a microprocessor, although discrete blocks are shown in FIG. 3). The controller operates various switches in the pacemaker, of which only two pairs are shown. Switches S2a, S2b are closed whenever the pacemaker is to pace or sense. In order to pace, a command on PACE conductor 26 is generated by the controller, with pulse generator 18 then applying a current pulse through switches S2a, S2b to the tip and ring electrodes. Sense amplifier 16 senses a cardiac signal on the electrodes. (Various functions well known in the art, such as blanking of the sense amplifier during pacing, are not shown inasmuch as they have no bearing on the subject invention.) The sensing of a heartbeat, spontaneous or evoked, results in a pulse appearing on LOAD conductor 24 extended to controller 28. The "load" function has to do with the loading of an initial value in timer 62 on FIG. 3, as will be described.

The impedance measurement is made when controller 28 pulses conductor 20 and informs block 14 that a measurement is required. At this time switches S1a, S1b close, and switches S2a, S2b open. A current is applied to the ring electrode 12, with the current flowing through the ring and the case. The case is shown symbolically by the numeral 30, and it serves as a reference potential for the pacemaker circuitry. The blood impedance is measured by block 14 determining the potential between tip electrode 10 and the case. Samples are derived at the rate of 20 per second, and digital samples are extended over conductor 22 to controller 28. The impedance measurement can be effected as described in the above-identified Nappholz et al patent.

Figure 2:
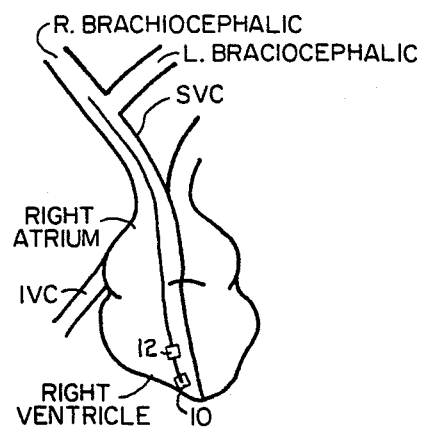
FIG. 2 depicts placement in a patient's right ventricle of a conventional bipolar lead which may be used to effect minute volume measurements, along with pacing and sensing.

Placement of the bipolar lead is as shown in FIG. 2. Tip electrode 10 is in contact with the wall of the right ventricle or right atrium of the patient. Ring electrode 12 is within the right ventricle. As described above, the impedance measurement reflects minute volume to a much greater extent than stroke volume because of the characteristics of the filter which is part of the impedance measurement circuit (see FIG. 1 of the Nappholz et al patent). In the preferred embodiment of the invention, the impedance signal is filtered by a two-pole filter whose center frequency is at 0.2 Hz. The gain is reduced by a factor of two (6 dB) at frequencies of 0.05 Hz and 0.8 Hz.

Digital samples are derived at the rate of 20 per second in the illustrative embodiment of the invention, and appear on conductor 22 in FIG. 3. Absolute magnitude extractor 40 derives the absolute magnitude of each digital sample. This simply means that negative signs are changed to positive. The average value of the digital samples is zero. This is because the filter in the impedance measurement block has a gain of zero for a frequency of zero (DC). By eliminating the sign from all samples, averager 42 derives a running average of the absolute magnitudes of the samples. The time constant of the averager is short so that the digital value at its output represents the average tidal volume over a few breaths. Adding the samples and averaging them provides a measure of the tidal volume because the absolute magnitudes represent the respiratory impedance signal.

Sign extractor 44 looks only at the sign of each sample. Successive bits are delivered to zero crossing detector 46, the bits representing the signs of the samples. The function of the zero crossing detector is to establish when the polarity of the measurement signal has changed. Whenever this happens, sampler 48 is triggered and a sample is taken of the average value represented by averager 42. This sample is delivered to both short-term averager 50 and long-term averager 52.

It should be noted that the zero crossing detector pulses its output twice during each breath, when the baseline is crossed during an exhalation and an inhalation. Thus two samples are taken for each breath. That is of no moment since what is desired are measurements which are representative of (proportional to) parameters of interest, not exact values. For such a scheme to work, it is important that the zero crossing detector function properly. Otherwise, too many or too few samples will be taken and the two averages derived by blocks 50 and 52 will not be accurate representations of short-term and long-term measurements. A type of "majority vote" technique is used to sense a zero crossing. In general, a zero crossing is assumed to have occurred when at least 60% of the most recent samples in the last 0.4–1.0 second have a sign opposite that of the signal after the last zero crossing. In the preferred embodiment of the invention, the requirement is that at least 70% of the most recent samples in the last 0.5 second have a sign opposite that of the signal after the last zero crossing.

As described above, simply integrating alternate cycles of a sinusoid (those of the same polarity), or integrating a rectified sinusoid, provides a value which is proportional to the amplitude of the sinusoid but does not reflect the frequency. The measurement technique disclosed in the Nappholz et al patent is efficacious, however, because the signal representative of breathing is not a sinusoid. Nevertheless, to the extent that there is a sinusoidal component in the signal, an integrative technique introduces some error. That error is not present when using the system of FIG. 3. Each average value sample at the output of averager 42 represents the average of the last few integrals of the respiratory impedance signal, i.e., tidal volume. The short-term averager and the long-term averager derive values which are dependent not only on the magnitudes of the samples delivered to them, but also on the rate at which the samples are delivered. (The respective time constants are slightly less than a minute and about one hour.) By delivering a sample every time that a zero crossing is detected, the rate of the breathing is also reflected in the short-term and long-term values of minute volume. The two significant aspects of the algorithm for deriving minute volume are that noise effects are eliminated from amplitude considerations by using an averager 42, and accurate sensing of zero crossings is assured by the majority-vote technique.

Figure 4A:
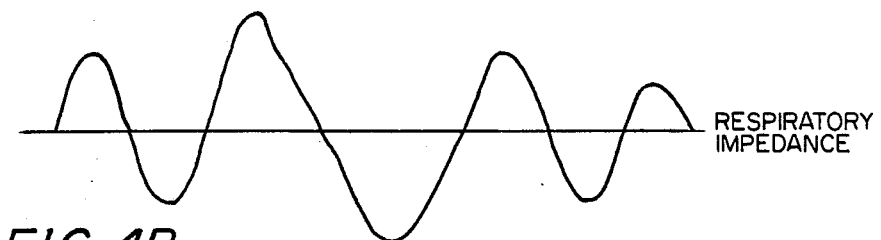
FIG. 4 depicts several waveforms which will facilitate an understanding of the operation of the circuitry of FIG. 3.
Figure 4B:
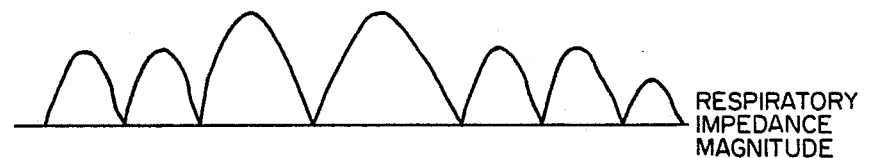
Figure 4C:
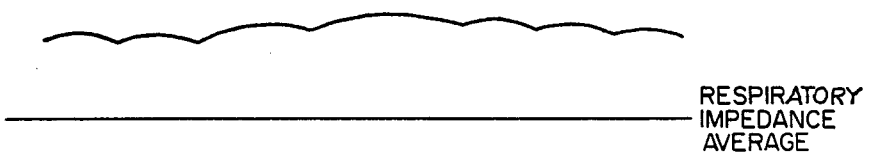
Figure 4D:
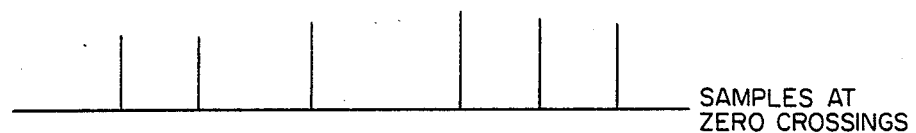
Figure 4E:

FIGS. 4A–4E depict the operation of the circuitry on the left side of FIG. 3. Waveform 4A is the respiratory impedance signal itself. The peak-to-peak amplitudes correspond to tidal volume. Waveform 4B shows the effect of rectifying the signal, that is, the effect of taking the absolute magnitude of the signal. Waveform 4C shows the average value, as a function of time, of the rectified impedance signal. Although such an analog signal is not developed in FIG. 3, averager 42 does derive a digital value which at any sampling time corresponds to the analog value shown in FIG. 4C. Periodically, whenever there is a zero crossing in the signal of FIG. 4A, a sample is taken; the sample values are represented by the vertical lines in FIG. 4D. Averaging the samples results in a step-like signal, as shown in FIG. 4E. The samples are applied to averager 50 and averager 52 in FIG. 3; the output of each of blocks 50 and 52 depends upon not only the amplitude of each sample at the input, but also the rate at which samples are applied and the time constant of the averager. (FIG. 4E shows the output of a generalized averager without concern for the two different time constants.)

Reference is made to a Technical Note entitled "Simple Impedance Pneumograph and Volume Integrator" at pp. 352–353 in the May 1973 issue of Medical and Biological Engineering. In that Technical Note, minute volume is measured by sampling peak values, and using a lowpass filter to integrate them. This should be contrasted with the technique of the invention in which tidal volume is estimated by measuring the average rectified value of the impedance signal, and zero crossings are used to estimate rate. Noise affects peak measurements much more significantly than it does an average value. [While a zero crossing detector is not necessarily more accurate than a peak detector, the zero crossing detector of the invention, based on a majority-vote technique, is more accurate than conventional zero crossing detectors.]

As indicated in FIG. 3, long-term averager 52 derives a value which represents minute volume as measured over an interval of about one hour. Short-term averager 50 derives a value which is based upon minute volume measurements during less than the last minute (e.g., 30 seconds). Summer 54 derives the difference between two signals, and it is represented in the drawing as delta MV. This is the control signal which drives the pacing rate. As the short-term average increases relative to the long-term average, representing metabolic demand, the pacing rate increases. Conversely, when the difference decreases, the pacing rate decreases.

The delta MV value at any instant is applied to the input of limiter 56. The other input to limiter 56 is delta MVMAX, a quantity which will be described below but which serves as the maximum delta MV value which can control the escape interval of the pacemaker. The current value of delta MV, or delta MVMAX if it is smaller than delta MV, is applied to the minus input of summer 58. A quantity referred to as maximum interval is applied to the plus input of the summer. Maximum interval is an offset which corresponds to the minimum rate of the pacemaker, a quantity set by the physician. The difference is applied to the input of timer 62. The timer is loaded with the difference value when a load signal is derived on conductor 24 by the sense amplifier of the pacemaker.

Clock 64 applies pulses to divider 66. The divider divides the clock pulses by a quantity referred to as prescaler; the net result is that pulses are applied to the decrement input of timer 62 at a rate slower than that of the clock itself. The count in timer 62 is decremented whenever a pulse appears at the output of divider 66. When the timer is decremented down to zero, a pulse appears on PACE conductor 26 to trigger pulse generator 18 in FIG. 1. If a spontaneous beat is sensed before the timer is decremented down to zero, a new value is loaded in timer 62 and a pacing pulse is not generated. It is in this manner that the pacemaker is made to operate in he standard VVI mode.

It will be apparent that as the quantity delta MV increases, the timer is loaded with a smaller value (maximum interval minus delta MV). This, in turn, means that the pacing rate increases, just what is required for a larger delta MV. When delta MV is zero, what gets loaded in the timer is simply the maximum interval. This results in the minimum rate, precisely what is required when there is no metabolic demand beyond that provided by the minimum pacing rate. The quantity maximum interval is thus simply the interval which corresponds to minimum rate, and conventional pacemakers are equipped with telemetry systems for allowing a physician to program minimum rate. The telemetry system 68 is shown in FIG. 3. Among other values (not shown), delta MV is transmitted from the pacemaker to a conventional type external programmer (not shown) for reasons to be described below. The programmer, in turn, programs four values which are required in the operation of the circuitry of FIG. 3. (Other values, such as pulse amplitude, can be programmed, as is known in the art, but are not pertinent to the present invention.) The prescaler value is also derived from the programmer, and it is applied to an input of divider 66. It is apparent that the larger the value of prescaler, the slower the rate at which timer 62 is decremented, and the longer the escape interval.

A third value which is derived from the programmer is delta MVMAX. This value corresponds to the maximum rate (another quantity which can be programmed in conventional pacemakers). How the several values are derived can only be understood by considering the overall programming procedure.

When a pacemaker is first implanted, the patient is put at rest for about one hour. A long-term average value of minute volume is derived by block 52 in the usual manner. The patient is then told to exercise until he is breathing at his peak rate. At this time the short-term average derived by block 50 will be at its maximum value for present conditions (those reflected in the long-term average). Thus the delta MV value at the output of summer 54 corresponds to the maximum control signal which will be used to control the pacing rate. It should be noted that in the short time that it takes the patient to get up to his peak exercising rate, the long-term value cannot change to any significant degree so that the delta MV value which is now derived indeed corresponds to peak metabolic demand. This value is telemetered out of the pacemaker, as shown at the bottom right of FIG. 3. The programmer measures the value and it is used as the delta MVMAX value which the programmer then telemeters back to the pacemaker.

The value, by itself, does not correspond to a maximum rate. It is simply the maximum value allowed for delta MV as an input to summer 58 during normal operation of the pacemaker. This is a form of runaway protection. Although there will be long-term changes, in the long run they will affect the short-term and long-term averages the same way, so the initially set value of delta MVMAX still applies no matter how the two average values are affected by long-term or permanent changes. (In the commercial Meta-MV pacemaker, the programmer can select from one of 60 values for delta MVMAX; it selects the one which is closest to the delta MV value which is telemetered out of the pacemaker during the set-up procedure.)

Clock 64 operates at a 32-kHz rate. As described above, the value of the prescaler determines the rate at which timer 62 is decremented. The pacing rate is inversely proportional to the initial value loaded in timer 62. Thus the pacing rate is inversely proportional to the difference between the maximum interval and the output of limiter 56. The pacing rate is also inversely proportional to the value of the prescaler because the larger the value, the less frequent the time-outs of timer 62. There are thus two equations which characterize the pacemaker operation in terms of the minimum rate desired by the physician and the maximum rate desired by the physician. The maximum rate is equal to some constant (which is a function of the clock rate) divided by a product of two factors. One factor is the prescaler value. The other factor is the difference between the maximum interval and delta MVMAX because for the maximum rate, the output of the limiter should be at its maximum (which is delta MVMAX). The other equation defines the minimum rate. The minimum rate is equal to the same constant divided by two factors. One of these factors is again the prescaler, and the other is simply the maximum interval; the minimum rate is obtained when delta MV is zero and the output of limiter 56 is zero. There are thus two equations and two unknowns, and the physician, or the programmer, can solve for the two quantities maximum interval and prescaler. These quantities are telemetered to the pacemaker for storage and subsequent control of the pacemaker operation.

It should be noted that maximum interval is not simply the inverse of the minimum rate. The term "maximum interval" as used herein is a quantity designed to provide minimum rate. But the actual value of that quantity depends on the solving of two equations for two unknowns. A physician may desire to provide the same minimum and maximum rates for two patients. During the set-up procedure, those two patients, when they are exercised, will have different delta MV values telemetered out of the pacemaker. The value telemetered out serves as the delta MVMAX value applied to limiter 56 in each case, and the two values are different. Since delta MVMAX is one input to summer 58, it is apparent that the quantity maximum interval must similarly be different for the two patients if they are to have the same minimum and maximum rates. It is the solution to two equations which allows the values maximum interval and prescaler to be derived for each patient.

The only remaining element on FIG. 3 not described thus far is comparator 60. The value of delta MV is fed to the plus input of the comparator, and the minus input of the comparator is fed by a reference threshold. This reference threshold is the fourth value programmed during the set-up procedure. Whenever delta MV exceeds a reference threshold, the output of the comparator goes high and inhibits long-term averager 52. What happens, in effect, is that a large value of delta MV is assumed to represent exercise. Until the patient stops exercising, the long-term average is not increased. Were it allowed to increase, after an hour or so it would approach the short-term average. As the long-term average increased, delta MV would keep getting smaller and the pacing rate would drop from its initial high value. Once the patient starts to exercise and the pacing rate increases, it is not desired that it decrease simply because time has elapsed. It is for this reason that the long-term average is frozen. Sooner or later when the patient stops exercising and the short-term average decreases, delta MV will be less than the reference threshold and the long-term average will be allowed to change in the usual manner. In the illustrative embodiment of the invention, the reference threshold is equal to one-half of delta MVMAX. The 50% level is not fixed, however, and can be programmed differently if desired by the physician. The general technique allows long-term adaptation to the minute volume measurement baseline while still allowing extended periods of exercise. In the illustrative embodiment of the invention, the threshold is midway between the minimum and maximum rates; in other words, if delta MV increases to the value which corresponds to the mid-range rate, the long-term average is frozen until delta MV drops below the mid-range value.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A rate-responsive pacemaker comprising means adapted to a patient's heart for pulsing at a controlled rate; a bipolar lead having tip and ring electrodes for coupling said pulsing means to the patient's heart, said pulsing means extending pacing current pulses to said tip electrode, said tip electrode being positionable on the heart wall and said ring electrode being positionable in a blood vessel in the vicinity of the patient's pleural cavity; means for periodically applying measuring current pulses between said ring electrode and a reference point in said pacemaker; means for measuring the blood impedance between said tip electrode and said reference point responsive to the application of a measuring current pulse between said ring electrode and said reference point, as the blood impedance varies as a function of the patient's pleural pressure; means responsive to said measuring means for determining the patient's minute volume; and means for changing said controlled rate in accordance with the patient's minute volume.

2. A rate-responsive pacemaker comprising means adapted to a patient's heart for pulsing at a controlled rate; a bipolar lead having tip and ring electrodes for coupling said pulsing means to the patient's heart; means for deriving a blood impedance signal by periodically introducing current pulses between said ring electrode and a reference point and measuring the voltage across said tip electrode and said reference point; said tip electrode being at a point in the patient's blood more distal from said reference point than said ring electrode; and means for adjusting said controlled rate as a function of said blood impedance signal.

3. A rate-responsive pacemaker in accordance with claim 2 wherein said adjusting means includes means for deriving a short-term average and means for deriving a long-term average of said blood impedance signal, means for deriving a difference between said short-term average and said long-term average, and means for varying said controlled rate in accordance with the derived difference.

4. A rate-responsive pacemaker in accordance with claim 3 further including means for inhibiting the deriving of said long-term average responsive to said derived difference exceeding a threshold value.

5. A rate-responsive pacemaker in accordance with claim 3 wherein said means for deriving said averages includes means for generating samples representative of an average value of said impedance signal over a relatively short interval, means for detecting zero crossings in said impedance signal, and means for controlling average means to up-date an average when a zero crossing is detected.

6. A responsive pacemaker in accordance with claim 5, wherein a period over which values are averaged to generate said short-term average and a period over which values are averaged to generate said long-term average differ by at least an order of magnitude.

7. A rate-responsive pacemaker comprising pulse generating means for generating pulses at a rate; means for coupling said pulse generating means to a patient's heart; means for monitoring a rate control parameter ("RCP"); means for deriving short-term and long-term values of said RCP; means for deriving a difference between said short-term and long-term RCP values and for adjusting the rate of said pulse generating means in accordance therewith; and means responsive to said difference exceeding a threshold value for inhibiting changes in said long-term RCP value.

8. A rate-responsive pacemaker in accordance with claim 7 wherein said threshold value is a programmable parameter.

9. A rate-responsive pacemaker in accordance with claim 7 wherein said coupling means is a bipolar lead, and said monitoring means monitors said RCP by performing an electrical measurement using said bipolar lead.

10. A method for determining a patient's minute volume from successive samples of a respiratory impedance signal comprising the steps of determining a zero crossing in the signal by comparing signs of successive samples, averaging the absolute magnitudes of each of successive samples to produce an absolute magnitude average, and averaging selected values of the absolute magnitude average with each selected value being the absolute magnitude average when a zero crossing occurs.

11. A method in accordance with claim 10 wherein the step of determining a zero crossing comprises ascertaining when at least 60 % of the most recent samples in the last 0.4–1.0 second have a sign opposite that of the signal after last zero crossing.

12. A method in accordance with claim 11 wherein said samples of said respiratory impedance signal are derived by sampling an electrical blood characteristic which is a function of pleural pressure over a bipolar pacemaker lead.

13. A method for determining a patient's minute volume from successive samples of a respiratory impedance signal comprising the steps of determining a zero crossing in the signal from the signs of successive samples, averaging the absolute magnitudes of successive samples, and averaging samples of said absolute magnitude average that the resulting average is proportional to the rate at which zero crossings occur.

14. A method in accordance with claim 13 wherein the step of determining a zero crossing comprises ascertaining when at least 60% of the most recent samples in the last 0.4–1.0 second have a sign opposite that of the signal after a last zero crossing.

15. A method in accordance with claim 13 wherein said samples of said respiratory impedance signal are derived by sampling an electrical blood characteristic which is a function of pleural pressure over a bipolar pacemaker lead.

16. A method for setting up a rate-responsive pacemaker having programmable parameters and which is equipped for two-way telemetry, the rate of the pacemaker being determined by a rate-control signal, comprising the steps of placing the patient at rest for an extended interval so that the patient adapts to a non-exercise state, suddenly causing the patient to exercise at a peak level so that the rate-control signal becomes a maximum and telemetering the value thereof to an external programmer, and programming parameter values by telemetering them from the programmer to the pacemaker, the parameter values being calculated as functions of both said maximum rate-control signal and rate values selected by a physician.

17. A method in accordance with claim 16 wherein said rate values selected by a physician are maximum rate and minimum rate.

18. A method in accordance with claim 16 where said rate-control signal is different for different patients even for the same pacemaker programmed parameters.

19. The rate responsive pacemaker of claim 2 wherein said reference point is the case of the pacemaker.

* * * * *